United States Patent [19]
McConnachie et al.

[11] Patent Number: 6,110,878
[45] Date of Patent: *Aug. 29, 2000

[54] LUBRICANT ADDITIVES

[75] Inventors: Jonathan M. McConnachie, Flemington; Edward Ira Stiefel, Bridgewater, both of N.J.; Ian Alexander Weston Bell, Southmoor; Velautha-Cumaran Arunasalam, Chertsey, both of United Kingdom

[73] Assignee: Exxon Chemical Patents Inc, Linden, N.J.

[*] Notice: This patent is subject to a terminal disclaimer.

[21] Appl. No.: 09/209,949

[22] Filed: Dec. 11, 1998

Related U.S. Application Data

[63] Continuation-in-part of application No. 08/990,053, Dec. 12, 1997, Pat. No. 5,906,968.

[51] Int. Cl.$^7$ .......................... C10M 139/00; C07F 11/00
[52] U.S. Cl. .......................... 508/363; 508/370; 508/379; 508/445; 556/25; 556/38; 556/57; 556/61
[58] Field of Search ...................... 508/363, 370, 508/379, 445; 556/25, 38, 57, 61

[56] References Cited

U.S. PATENT DOCUMENTS

| | | | |
|---|---|---|---|
| 5,631,213 | 5/1997 | Tanaka et al. | 508/363 |
| 5,688,748 | 11/1997 | Tomizawa | 508/363 |
| 5,888,945 | 3/1999 | Stiefel et al. | 508/363 |
| 5,895,779 | 4/1999 | Boffa | 508/555 |
| 5,906,968 | 5/1999 | McConnachie et al. | 508/363 |

*Primary Examiner*—Jerry D. Johnson

[57] ABSTRACT

Oil-soluble or oil-dispersible trinuclear molybdenum-sulfur compounds are made by reacting less than three, such as 1.5 to 2.5, preferably two to 2.1, molar equivalents of a disulfide with one molar equivalent of a compound containing the $[Mo_3S_{13}]^{2-}$ ion. The trinuclear compounds include S-containing ligands that are derived from the disulfide reactant via cleavage of the disulfide bond; the ligands are bound to the core via the S atoms.

8 Claims, No Drawings

LUBRICANT ADDITIVES

This is a division, of application Ser. No. 08/990,053 filed Dec. 12, 1997 now U.S. Pat. No. 5,906,968

The invention relates to a method of making trinuclear molybdenum-sulfur compounds.

New lubricant additives that possess antifriction, antiwear and antioxidant properties are continually needed. Some molybdenum compounds possess one or more of these properties; International Patent Application No. PCT/IB97/01656 describes trinuclear molybdenum-sulfur compounds as lubricant additives.

The above-mentioned International Patent Application describes making trinuclear molybdenum—sulfur compounds of the formula $Mo_3S_xL_y$, wherein L is dihydrocarbyldithiocarbamate, x is 4 to 10 and y is 4, using three molar equivalents of thiuram disulfide to one molar equivalent of $(NH_4)_2Mo_3S_{13}.2H_2O$. This reaction undesirably results in the formation of two molar equivalents of a by-product of the formula $NH_4L_y$ that must be removed or further treated in order to reduce the incompatibility of the product with seals and corrosivity to copper.

Beneficially, the present invention, by decreasing the amount of ligand source that is required as a starting material, produces an absence or an essential absence of such undesired by-product in the product, and solves the above problem.

In a first aspect, the invention is a method of making an oil-soluble or oil-dispersible trinuclear molybdenum-sulfur compound comprising a trinuclear molybdenum core bonded to ligands capable of rendering the compound oil-soluble or oil-dispersible one or more of the ligands, preferably each ligand, containing a S atom via which it is bonded to the core, which method comprises reacting (A) one molar equivalent of a reactant compound containing an anion that contains a trinuclear molybdenum core, such as a thio- or polythio-trinuclear molybdenum core, for example the $[Mo_3S_{13}]^{2-}$ ion, and (B) less than 3, such as 1.5 to 2.5, preferably 2 to 2.1, molar equivalents of an organic disulfide, from which said one or more ligands is or are derived, to produce said trinuclear compound.

Without wishing to be bound by any theory, it is believed that, in the reaction, the S—S bond of the disulfide cleaves so that each S atom and its attendant residue of atoms bonded thereto forms said one or more ligands. Preferably, the disulfide is a bis(disulfide).

Preferably, two molar equivalents of the disulfide are used in the method of invention.

In a second aspect, the invention is a lubricating oil composition comprising a major amount of an oil of lubricating viscosity and a minor amount of a trinuclear molybdenum-sulfur compound made by the method of the first aspect.

In a third aspect, the invention is a method of making a lubricating oil composition comprising blending a major amount of an oil of lubricating viscosity and a minor amount of a trinuclear molybdenum-sulfur compound made by the method of the first aspect.

In a fourth aspect, the invention is a method of lubricating an internal combustion engine comprising supplying to the engine a lubricating oil composition of the second aspect or made by the method of the third aspect.

In a fifth aspect, the invention is a method for reducing one or more of the friction, wear and oxidancy, and retention of these properties, of an internal combustion engine comprising treating moving surfaces thereof with a lubricating oil composition of the second aspect or made by the method of the third aspect.

In a sixth aspect, the invention is a method for reducing the fuel consumption of an internal combustion engine, and retention of the property, comprising treating moving surfaces thereof with a lubricating oil composition of the second aspect or made by the method of the third aspect.

The features of the invention will now be discussed in more detail.

The compounds made by the present invention have, as stated above, a trinuclear molybdenum-sulfur core to which the ligands are bonded. They may, for example, have the formula $Mo_3S_xL_y$ wherein x is from 4 to 10, such as 4 to 7, preferably 4 or 7;

L represents the ligands; and y is a number to neutralise the charge on the $Mo_3S_x$ core, such as 4 when L is monovalent.

By "bonded" in this specification is meant to include covalent bonding, bonding by electrostatic interaction as in the case of a counter-ion, and forms of bonding intermediate between covalent and electrostatic bonding. Ligands within the same compound may be differently bonded. For example, when y is 4, three of L may be covalently bonded and the fourth of L electrostatically bonded.

The disulfide may be represented by the formula $Res^1$—S—S—$Res^2$ wherein $Res^1$ and $Res^2$ represent residues of the disulfide molecule which may be the same or different, preferably the same. Thus, the ligands in the compounds made by the method of the invention may be represented by the formulae $Res^1$—S— and $Res^2$—S—.

Preferably, each of $Res^1$ and $Res^2$ may be represented by a formula selected from the formulae I to III depicted below:

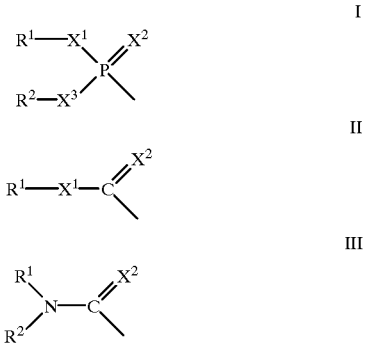

in which formulae, each of $R^1$ and $R^2$ independently represents a hydrocarbyl group or a hydrogen atom, provided that at least one hydrocarbyl group is present in the disulfide to confer oil-solubility or oil-dispersability on the trinuclear molybdenum compound; and each of $X^1$, $X^2$ and $X^3$ independently represents an oxygen atom or a sulfur atom.

Examples of disulfides for use in the present invention are hydrocarbyl substituted thiuram disulfides such as a di- or tetrahydrocarbyl thiuram disulfide; bis (dihydrocarbyl dithio-phosphonate) disulfides; bis (dithiohydrocarbyl dithio-phosphonate) disulfides; hydrocarbyl-substituted xanthogens; or hydrocarbyl-substituted thioxanthogens, of which tetrahydrocarbyl thiuram disulfides are preferred. When the latter are used, the ligands will be dithiocarbamate ("dtc") ligands.

The term "hydrocarbyl" denotes a substituent having a carbon atom directly attached to the remainder of the residue and hence to a ligand in the product and is predominantly hydrocarbyl in character within the context of this invention Such substituents include the following: (1) hydrocarbon substituents, that is, aliphatic (for example alkyl or alkenyl), alicyclic (for example cycloalkyl or cycloalkenyl) substituents, aromatic-, aliphatic- and alicyclic-substituted aromatic nuclei, as well as cyclic substituents wherein the ring is completed through another portion or the residue (that is, any two indicated substituents may together form an alicyclic group); (2) substituted hydrocarbon substituents, that is, those containing non-hydrocarbon groups which, in the context of this invention, do not alter the predominantly hydrocarbyl character of the substituent. Those skilled in the art will be aware of suitable groups (e.g., halo, (especially chloro and fluoro), amino, alkoxyl, mercapto, alkylmercapto, nitro, nitroso and sulfoxy); (3) hetero substituents, that is, substituents which, while predominantly hydrocarbon in character within the context of this invention, contain atoms other than carbon present in a chain or ring otherwise composed of carbon atoms.

The hydrocarbyl groups are preferably alkyl (e.g., in which the carbon atom attached to the remainder of the ligand is primary, secondary or tertiary), aryl, substituted aryl and ether groups.

Importantly, the hydrocarbyl groups have a sufficient number of carbon atoms to render the compounds soluble or dispersible in oil The compounds' oil solubility or dispersibility may be influenced by the number of carbon atoms in the ligands. Preferably the ligands have a sufficient number of carbon atoms to render the compound soluble or dispersible in oil. The total number of carbon atoms present among all of the hydrocarbyl groups of the compounds' ligands typically will be at least 21, e.g., 21 to 800, such as at least 25, at least 30 or at least 35. For example, the number of carbon atoms in each alkyl group will generally range between 1 to 100, preferably 1 to 40, and more preferably between 3 and 20.

An example of a reactant compound in the method of the invention is an ammonium salt of the anion such as $(NH_4)_2Mo_3S_{13}.nH_2O$ wherein n is 0 to 2, including non-integer values. The reaction may be carried out at elevated temperature, typically 60° C. to 150° C. The reaction may be carried out in an inert atmosphere such as of argon or nitrogen; it may also be carried out in the presence of an oxidizing source such as air, hydrogen peroxide or oxygen. The reaction may be carried out in the presence of a sulfur-abstracting agent such as triphenyl phosphine, a cyanide or a sulfite.

The resulting product, such as $Mo_3S_xL_y$, in the reaction mixture may be isolated. Any excess of the reactant compound containing the anion resulting from the method of the present invention may, if desired, be removed such as by filtration.

The reaction may be carried out in a suitable organic solvent which may be removed from the product such as by distillation after the reaction has taken place. To lessen the risk of thermally degrading the product during distillation, it may be appropriate to use, as solvent, a low boiling point organic liquid such as methanol which may be distilled at a lower temperature than solvents of higher boiling point.

The reaction product may be useful as a multifunctional lubricating oil additive having enhanced antifriction, antiwear and antioxidant properties and may be used to enhance antifriction, antiwear and antioxidancy properties of an oil of lubricating viscosity by adding the reaction product thereto to produce a lubricating oil composition.

Other additives such as known in the art may be incorporated, provided they are different from those of the invention. Examples are dispersants, detergents, rust inhibitors, anti-wear agents, antioxidants, corrosion inhibitors, friction modifiers, pour point depressants, anti-foaming agents, viscosity modifiers and surfactants.

In the preparation of lubricating oil compositions, it is common practice to introduce additive(s) therefor in the form of concentrates of the additive(s) in a suitable oleaginous, typically hydrocarbon, carrier fluid, e.g. mineral lubricating oil, or other suitable solvent. Oils of lubricating viscosity as well as aliphatic, naphthenic, and aromatic hydrocarbons are examples of suitable carrier fluids for concentrates. Concentrates constitute a convenient means of handling additives before their use, as well as facilitating solution or dispersion of additive in lubricating oil compositions. When preparing a lubricating oil composition that contains more than one type of additive (sometimes referred to as "additive components"), each additive may be incorporated separately—each in the form of a concentrate. In may instances, however, it is convenient to provide a so-called additive "package" (also referred to as an "adpack") comprising two or more additives in a single concentrate.

A concentrate may contain 1 to 90, such as 10 to 80, preferably 20 to 80, more preferably 20 to 70, mass % active ingredient of the additive or additives.

Lubricating oil compositions may be prepared by adding to an oil of lubricating viscosity a mixture of an effective minor amount of at least one additive and, if necessary, one or more co-additives such as described herein. The preparation may be accomplished by adding the additive directly to the oil or by adding it in the form of a concentrate thereof to disperse or dissolve the additive. Additives may be added to the oil by any method known to those skilled in the art, either prior to, contemporaneously with, or subsequent to addition of other additives.

EXAMPLES

The invention may be demonstrated with reference to the following examples.

As used herein "coco" is an alkyl chain or mixture of alkyl chains of varying even numbers of carbon atoms, typically from $C_6$ to $C_{18}$.

Example 1

Synthesis of $Mo_3S_7(dtc)_4$ from two molar equivalents of thiuram disulfide ("TDS") per molar equivalent of a trinuclear molybdenum compound under an inert atmosphere was carried out by placing $(NH_4)_2Mo_3S_{13}.2H_2O$ (7.76 g 10 mmol) and tetracocothiuram disulfide (19.5 g, 20 mmol) in a flask which was evacuated and filled three times with Ar. Oxygen-free toluene (50 mL) and methanol (50 mL) were added to the flask and the solvents were degassed. The solution was refluxed vigorously for eight hours. The solvents were then removed by distillation under reduced pressure. The product was dissolved in heptane and filtered. The heptane was then removed by distillation under reduced pressure to yield approximately 25 g of $Mo_3S_7(dtc)_4$.

Example 2

Synthesis of $Mo_3S_7(dtc)_4$ was carried out by the procedure of Example 1 but incorporating an $air/O_2$ purge. Thus, air was purged through the solution when it was refluxed vigorously for eight hours. The product was approximately 25 g of $Mo_3S_7 (dtc)_4$.

TESTS

Three molybdenum-containing oils were tested for friction retention properties by comparing the High Frequency Reciprocating Rig (HFRR) performance of the oils when fresh with that of the oils when aged. The oils were aged by treatment with 1% $NO_2$ in air at 60 ml/min at 150° C. for 24 hours. The friction properties were then recorded at 140° C. and compared with the results from the fresh oils. Three oils were compared by this method, each containing corresponding amounts (500 ppm) of molybdenum from three different molybdenum sources. The molybdenum components were MV822, a commercial dinuclear component; $Mo_3S_7dtc_4$ made by using three molar equivalents of thiuram disulfide (TDS) as described in International Patent Application No PCT/IB97101656 (METHOD A); and $Mo_3S_7dtc_4$ made by the method of the present invention using two molar equivalents of TDS (METHOD 1). The results of these tests are shown in Table 1 below. Both of the trinuclear molybdenum compound-containing oils showed better friction retention properties than the oil containing the dinuclear molybdenum compound. Also, oils containing trinuclear molybdenum compounds made by different methods give comparable performances in the tests.

TABLE 1

| Molybdenum compound (@ 500 ppm) | MV822 | METHOD A $Mo_3S_7dtc_4$ | METHOD 1 $Mo_3S_7dtc_4$ |
| --- | --- | --- | --- |
| coefficient of friction for fresh oil | 0.096 | 0.086 | 0.095 |
| coefficient of friction for used oil | 0.158 | 0.079 | 0.084 |

What is claimed is:

1. A method of making an oil-soluble or oil-dispersible trinuclear molybdenum-sulfur compound comprising a trinuclear molybdenum core bonded to ligands capable of rendering the compound oil-soluble or oil-dispersible, one or more of the ligands containing a S atom, via which it is bonded to the core,—which method comprises reacting (A) one molar equivalent of a reactant compound containing an anion that contains a trinuclear molybdenum core and (B) less than 3 molar equivalents of a organic disulfide from which said one or more ligands is or are derived, to produce said trinuclear compound.

2. The method as claimed in claim 1 wherein the reactant compound contains the $[Mo_3S_{13}]^{2-}$ ion.

3. The method as claimed in claim 1 wherein two molar equivalents of the disulfide are reacted.

4. The method as claimed in claim 1 wherein the trinuclear molybdenum compound has the formula $Mo_3S_xL_y$ wherein
    x is a numeral of from 4 to 10,
    L represents the ligands, and
    y is a number to neutralise the charge on the $Mo_3S_x$ core.

5. The method as claimed in claim 1 wherein the disulfide is a tetrahydrocarbyl thiuram disulfide; a bis (dihydrocarbyl dithio-phosphonate) disulfide; a bis (dithiohydrocarbyl dithio-phosphonate)disulfide; a hydrocarbyl-substituted xanthogen; or a hydrocarbyl-substituted thioxanthogen.

6. The method as claimed in claim 5 wherein the hydrocarbyl groups are alkyl groups.

7. The method as claimed in claim 6 wherein the alkyl groups have from 3 to 20 carbon atoms.

8. The method as claimed in claim 1 wherein each ligand contains an S atom, the trinuclear molybdenum core of the reactant containing an anion is a thio- or polythio-trinuclear molybdenum core, and the molar equivalent of organic disulfide is from about 2 to 2.1.

* * * * *